(12) United States Patent
Gerber

(10) Patent No.: US 10,842,909 B2
(45) Date of Patent: Nov. 24, 2020

(54) SILICIC ACID CONDENSATES HAVING A LOW DEGREE OF CROSS-LINKING IN A POLYMER MATRIX

(71) Applicant: Thomas Gerber, Sildemow (DE)

(72) Inventor: Thomas Gerber, Sildemow (DE)

(*) Notice: Subject to any disclaimer, the term of this patent is extended or adjusted under 35 U.S.C. 154(b) by 0 days.

(21) Appl. No.: 16/057,611

(22) Filed: Aug. 7, 2018

(65) Prior Publication Data

US 2018/0344895 A1 Dec. 6, 2018

Related U.S. Application Data

(62) Division of application No. 13/981,598, filed as application No. PCT/EP2012/051581 on Jan. 31, 2012, now Pat. No. 10,064,974.

(30) Foreign Application Priority Data

Jan. 31, 2011 (DE) .................. 10 2011 009 838
Jan. 31, 2011 (DE) .................. 10 2011 009 839

(51) Int. Cl.
*A61L 26/00* (2006.01)
*C01B 33/145* (2006.01)
(Continued)

(52) U.S. Cl.
CPC ....... *A61L 26/0004* (2013.01); *A61L 26/0095* (2013.01); *A61L 27/025* (2013.01);
(Continued)

(58) Field of Classification Search
CPC .................................................. A61L 26/0095
See application file for complete search history.

(56) References Cited

U.S. PATENT DOCUMENTS 5,914,162 A * 6/1999 Bilkadi ...................... C09J 7/28
428/35.8
10,064,974 B2 9/2018 Gerber
(Continued)

FOREIGN PATENT DOCUMENTS

CN 101786139 A 7/2010
JP 02248331 A 10/1990
(Continued)

OTHER PUBLICATIONS

English translation of Hayashi et al. (JP2-248331); Phoenix Translations; Jun. 2015.
(Continued)

*Primary Examiner* — Michael F Pepitone
(74) *Attorney, Agent, or Firm* — Kilpatrick Townsend & Stockton LLP

(57) ABSTRACT

A material or biomaterial comprising silicic acid condensates having a low degree of cross-linking, and methods for its production are subject-matter of the invention. A method for the production of silicic acid structures having a low degree of cross-linking is disclosed, wherein a sol is produced, wherein further condensation is prevented when specific cross-linking of the silicic acid is reached, wherein, preferably, structures having a size of 0.5-1000 nm are produced, e.g. polyhedral structures or aggregates of the same. Further condensation can be prevented by means of mixing with a polymer. In one embodiment, this comprises nano-structured, silicon dioxide ($SiO_2$) having a low degree of cross-linking that is embedded in a polymer matrix. The material can be used in medicine for therapeutic purposes, and can enter into direct contact with biological tissue of the body in this connection. This material herein enters into chemical, physical, and biological interactions with the corresponding biological systems. It can herein be decomposed, and can act as a supplier for the silicic acid required (Continued)

for metabolism. Furthermore, it can have a supportive or shielding effect. It can be present as a granulate, microparticles, fiber, and as a woven or nonwoven fabric produced therefrom, or as a layer on implants or wound dressings. The material can be used as a medical device or as a nutritional supplement.

19 Claims, 1 Drawing Sheet

(51) Int. Cl.
C01B 33/148 (2006.01)
A61L 27/48 (2006.01)
A61L 27/44 (2006.01)
A61L 27/02 (2006.01)

(52) U.S. Cl.
CPC ............. *A61L 27/446* (2013.01); *A61L 27/48* (2013.01); *C01B 33/145* (2013.01); *C01B 33/1485* (2013.01); *A61L 2430/02* (2013.01); *Y10T 428/298* (2015.01); *Y10T 428/2982* (2015.01)

(56) References Cited

U.S. PATENT DOCUMENTS

2008/0076838 A1* 3/2008 Puppe .................. C01B 33/148
516/34

2008/0185041 A1* 8/2008 Sharma ................ C03C 17/009
136/261

FOREIGN PATENT DOCUMENTS

| WO | WO 2001/52618 A2 | 7/2001 |
| WO | WO 2005/087284 A2 | 9/2005 |
| WO | WO 2006/128793 A1 | 12/2006 |
| WO | WO 2009/020919 A2 | 3/2009 |

OTHER PUBLICATIONS

Database WPI, Week May 8, 2010, Silicasol for polymer modification, has alkaline silicasol and predetermined mass percentage etc.; Thomson Scientific, London, GB; AN 2010-L26448.
Final Office Action dated Jun. 6, 2016 in U.S. Appl. No. 13/981,598. 10 pages.
Non-Final Office Action dated May 17, 2017 in U.S. Appl. No. 13/981,598. 8 pages.
Non-Final Office Action dated Aug. 14, 2015 in U.S. Appl. No. 13/981,598. 11 pages.
Notice of Allowance dated May 17, 2018 in U.S. Appl. No. 13/981,598. 7 pages.
Ex Parte Quayle Action dated Mar. 9, 2018 in U.S. Appl. No. 13/981,598, 5 pages.

* cited by examiner

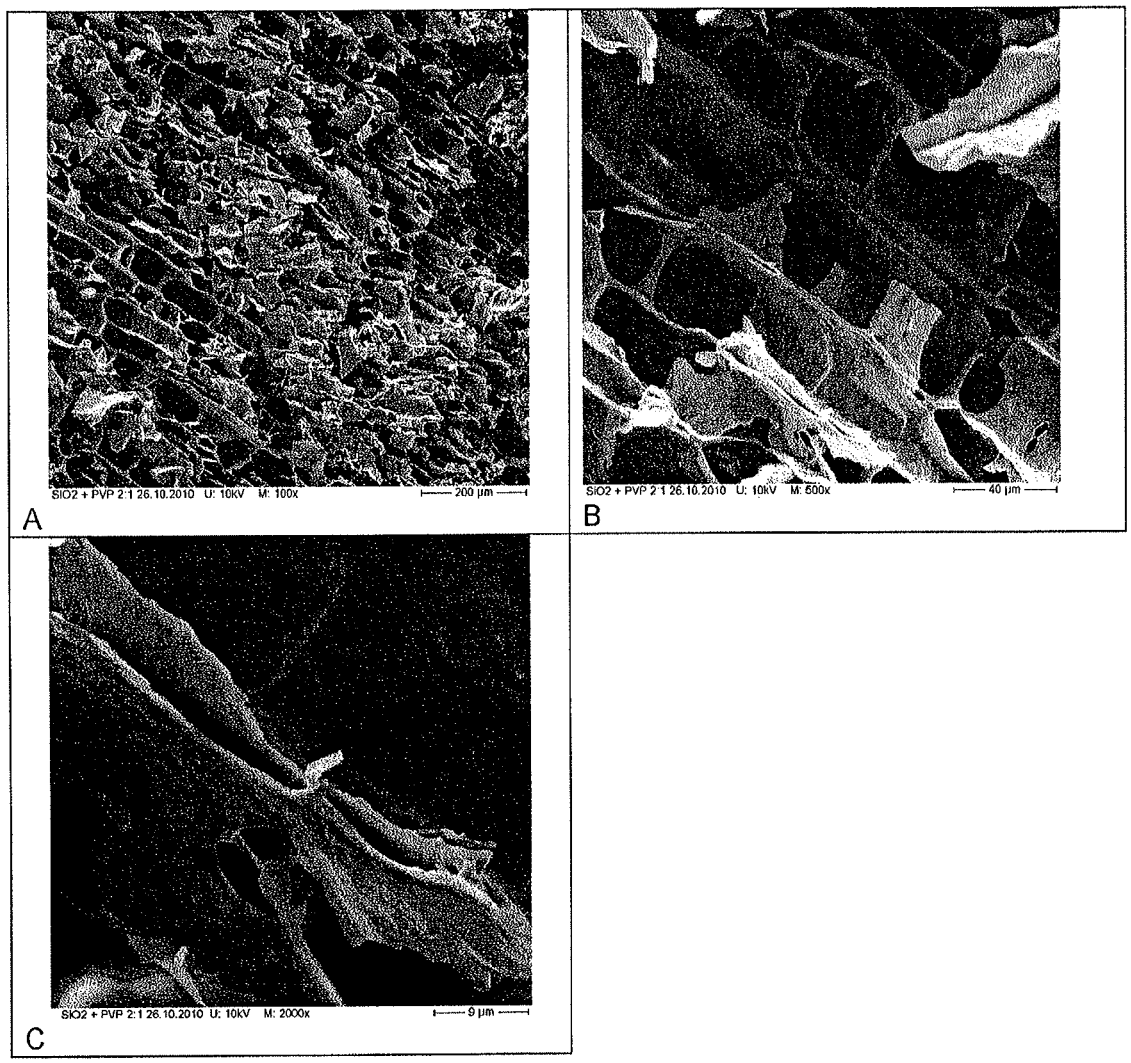

SILICIC ACID CONDENSATES HAVING A LOW DEGREE OF CROSS-LINKING IN A POLYMER MATRIX

CROSS-REFERENCE TO RELATED APPLICATIONS

This application is a divisional application of U.S. application Ser. No. 13/981,598, filed Oct. 7, 2013 (now U.S. Pat. No. 10,064,974), which is a national phase application under 35 U.S.C. 371 claiming priority to PCT/EP2012/051581, filed Jan. 31, 2012, which application claims priority to DE 102011009839, filed Jan. 31, 2011, and DE 102011009838, filed Jan. 31, 2011, the teachings of which are hereby incorporated by reference in their entireties for all purposes.

DETAILED DESCRIPTION OF THE INVENTION

A material or biomaterial comprising silicic acid condensates having a low degree of cross-linking, and methods of producing the same are subject matter of the present invention. A method for the production of silicic acid structures having a low degree of cross-linking is disclosed, in which a sol is produced, wherein further condensation is prevented once a specific degree of cross-linking of the silicic acid is reached, wherein, preferably, structures having a size of 0.5-1000 nm are produced, for example polyhedral structures or aggregates thereof. Further condensation can be prevented by mixing with a polymer. In one embodiment, this comprises nanostructured, silicon dioxide ($SiO_2$) having a low degree of cross-linking that is embedded in a polymer matrix. The material can be used in medicine for therapeutic purposes, and, in this connection, can enter into direct contact with biological tissue of the body. When this happens, this material enters into chemical, physical and biological interactions with the corresponding biological systems. In this connection, it can be decomposed and can act as a supplier of the silicic acid needed in metabolism. Furthermore, it can have a supportive or shielding effect. It can be present as a granulate, microparticles, fiber, and woven or nonwoven fabric produced therefrom, or as a layer on implants or wound dressings. The material can be used as a medical device or as a nutritional supplement.

Since the 70s of the past century, it is known that silicon is an important trace element for building bones and collagen (see, for example, M. Carlisle; Silicon: An Essential Element for the Chick; *Science* 10 Nov. 1972: Vol. 178. no. 4061, pp. 619-621). The precise biochemical processes continue to be unknown. In the metabolism, silicon primarily occurs as silicon dioxide. It is also not known in what structure the silicon dioxide best participates in the metabolism. Silicon dioxide occurs as a crystalline compound (e.g. quartz, cristobalite), as glass and as an amorphous substance. In crystal and in glass, the silicon is determined by almost complete cross-linking of the $SiO_{4/2}$ tetrahedrals. Amorphous silicon dioxide with the significant representative of silica gel, in contrast, has a network that is not continuous and that is characterized by more or less internal surface with open bonds (mostly SiOH).

With regard to degradation of silicon dioxide, the solubility of silicon dioxide in water in the range of physiological pH is of interest. For amorphous $SiO_2$ at pH 7, it lies at approximately 150 ppm. In contact with living tissue, dissolution takes place more quickly than in buffer solution pH 7.4. The reason for this is unknown (Iler, The Chemistry of Silica, 1979, John Wiley & Sons).

For wound dressings, in patent US005741509A, mixing of silicone medium with "fumed silica" is described. "Fumed silica" consists of non-porous $SiO_2$ particles having a density of 2.2 g/cm$^3$ and a size between 5 and 50 nm (Wikipedia). The density, which is identical to that of silica glass, just like the absence of porosity, shows that these are completely cross-linked $SiO_2$ structures.

In patent US2004/0235574A1, mixing of silicone medium with "fumed silica" is described, wherein additionally, substances having an antibacterial effect are added.

U.S. Pat. No. 7,074,981 B2 describes a wound dressing in which an absorbent or an adsorbent in the form of silica gel is used. An absorbent or an adsorbent composed of silica gel is, according to the state of the art, a xerogel, which is generally produced from sodium silicate solution, where cross-linking of the $SiO_2$ structures that is typical for a xerogel takes place. (Under Wikipedia "Adsorption": "Silica gel is a chemically inert, nontoxic, polar and dimensionally stable (<400° C. or 750° F.) amorphous form of $SiO_2$. It is prepared by the reaction between sodium silicate and acetic acid, which is followed by a series of after-treatment processes such as aging, pickling, etc. These after-treatment methods result in various pore size distributions.")

Patent DE 196 09 551 C1 concerns itself with biologically degradable fibers, composed of $SiO_2$, among other things, their production and their use as reinforcement fibers. Here, the production of a sol that can be spun is described. The method described and the application described are based on a diploma thesis by Monika Kursawe from 1995. The thesis in turn is based on the original synthesis instructions of Sakka from 1982 (S. Sakka, K. Kamiya; J. Non-Cryst. Solids 48, 1982 31). Sakka describes a method in which gel threads are spun, from which glass fibers are then produced in a later step. The starting material is tetraethylorthosilicate (TEOS), wherein a sol that can be spun is produced by means of hydrolysis and condensation. Sakka already shows that only a limited range in the composition (TEOS, $H_2O$, solvent (generally ethanol) and catalyst) leads to sols that can be spun, as a result of the thixotropic properties of the sols. In particular, the molar ratio of water to TEOS must lie around $r_w$ 2.

In the dissertation "Development of a method for the production of degradable silica gel fibers for medical technology" (Monika Kursawe 1999), a further development of the 1995 thesis of Kursawe, it is stated that the most important difference between the method described in her thesis and the method of Sakka is that after condensation, sol maturation was introduced, and that nitric acid was used as a catalyst instead of hydrochloric acid. In the dissertation, the method is then optimized in such a manner that the production of high-quality silica gel fibers in larger amounts can take place. The process is based on the slightly modified synthesis instruction of Sakka described in the thesis.

Patent DE 37 80 954 T2 describes a method of silicon dioxide glass fibers, wherein, here, too, the basic method of Sakka was modified.

Patent DE 10 2007 061 873 A1 describes the production of a silica sol material and its use as a biologically resorbable material. Patent DE 19609551C1 is referred to as prior art. As a distinction from this patent, it is stated that here that the fibers do not achieve optimal results in cytotoxicity tests after spinning; the causes for this can be many and are not related to the essential method steps. The second distinction, that a "solid phase" is formed according to DE 10 2007 061 873 A1, which brings about compulsory filtering of the sol, is also not brought into relation with the essential method steps. The main claim 1 of patent DE 10 2007 061 873 A1 essentially reproduces the production instructions that M. Kusawe describes in her dissertation (1999) and that were also published in her thesis in 1995. M. Kusawe divides the production of sol that can be spun into "hydrolysis," "condensation," and "maturation." According to Kusawe, "condensation" is characterized in that ethanol is withdrawn from the sol. This corresponds to claim 1 b) of the patent DE 10 2007 061 873 A1. In Kusawe, "maturation" takes place at 5° C., in her standard approach. This in turn corresponds to claims 1 c) and 1 d). In the example of the patent DE 10 2007 061 873 A1, maturation is conducted at 4° C. In terms of the other essentially parameters, as well, the example corresponds to the standard approach of Kusawe (e.g. molar ratio of water/TEOS 1.75, in Kusawe 1.8). The methods for the production of sols that can be spun of patents DE 196 09 551 C1 and DE 10 2007 061 873 A1, in terms of their essential steps, do not go beyond the level of knowledge of the thesis of Kusawe from 1995. The thesis is also strongly based on the level of knowledge of Sakka from 1982 (S. Sakka, K. Kamiya; J. Non-Cryst. Solids 48, 1982 31).

It is the task of the present invention to optimize the structure of silicic acid condensation products in such a manner that controlled degradation can take place in in vivo application, and that these silicic acid condensation products can be present in specific application forms such as granulate, microparticles, fibers, or as layers on implants or wound dressings. Production methods are to be made available for this purpose.

According to the invention, this task is accomplished in that the condensation of the silicic acid is controlled in aqueous or in alcoholic solution in such a manner that defined polyhedral structures are formed and that these polyhedral structures are maintained during the subsequent method steps such as, for example, removal of the solvent. The goal is to produce silicic acid structures having a low degree of cross-linking, which are characterized in that they are not integrated into a continuous network like the fused silica network. In this connection, the lowest degree of cross-linking is represented by a polyhedral composed of $SiO_2$ tetrahedrals, where five-, six- and seven-rings form a spatial structure of approximately 0.5 nm diameter. Such structures are described in: B. Himmel, Th. Gerber and H. Burger: WAXS- and SAXS-investigations of structure formation in alcoholic $SiO_2$ solutions, Journal of Non-Crystalline Solids, Amsterdam, 119 (1990) 1-13; B. Himmel, Th. Gerber and H. Burger: X-ray diffraction investigations of silica gel structures, Journal of Non-Crystalline Solids, Amsterdam, 91 (1987) 122-136; B. Himmel, Th. Gerber, W. Heyer and W. Blau: X-ray diffraction analysis of $SiO_2$ structure, Journal of Material Science, Chapman and Hall Ltd., London, 22 (1987) 1374-1378; Th. Gerber and B. Himmel: The structure of silica glass in dependence on the fictive temperature, Journal of Non-Crystalline Solids, Amsterdam, 92 (1987) 407-417; Th. Gerber and B. Himmel: The structure of silica glass, Journal of Non-Crystalline Solids, Amsterdam, 83 (1986) 324-334; B. Himmel, Th. Gerber and H.-G. Neumann: X-ray diffraction investigations of differently prepared amorphous silicas, Physica Status Solidi (a), 88 (1985) K127-K130).

One starting material for the production of silicic acid condensation products is tetraethylorthosilicate (TEOS). Silicic acid is formed with water, in the presence of a catalyst, wherein the molar ratio of water/TEOS must be at least 4 in order to achieve complete hydrolysis at the starting point. The mono-silicic acid that is formed condenses and forms polyhedral structures of approximately 0.5 nm-1 nm, called primary particles, which then form fractal clusters in a cluster-cluster aggregation. These clusters grow as a result of the aggregation process, and, at a specific size of the clusters, gel formation occurs. In other words, the clusters fill the container as a result of their packing or by means of the percolation network that has formed (Th. Gerber, B. Himmel and C. Hubert: WAXS and SAXS investigation of structure formation of gels from sodium water glass, Journal of Non-Crystalline Solids, (1994) Vol. 175, p. 160-168 and B. Knoblich, Th. Gerber. C. F. Brinker and G. W. Scherer describe gel formation in an extra chapter in "Sol-gel-science: The physics and chemistry of sol-gel processing" (Academic Press; San Diego; 1990). Gel formation is characterized by an extreme increase in viscosity.

These or analogous structures can be produced on the basis of sodium silicate solution. In this connection, the sodium ions are preferably removed from the solution using an ion exchanger. The remaining silicic acid here is then already present as a condensation product. These are polyhedral structures having a size of approximately 0.5 nm, once again called primary particles, which then form fractal clusters as a function of the pH, by means of aggregation, which in turn lead to gel formation (B. Knoblich, Th. Gerber: Aggregation in $SiO_2$ sols from sodium silicate solutions, Journal of Non-Crystalline Solids 283 (2001) 109-113).

The aggregation clusters (solid scaffolding, metal oxide) of the alcogel (solvent, alcohol) or hydrogel (solvent, water) are destroyed during drying by the capillary forces that are in effect and by the condensation of the internal surface that takes place ($2Si_{surface}$—OH→$Si_{bulk}$—O-$M_{bulk}$+$H_2O$). A xerogel is formed, the internal surface of which lies, for example, in the case of $SiO_2$, in the range of 25-700 $m^2/g$, and the density of which lies in the range above 1.0 $g/cm^3$. The defined polyhedral structures in the primary particles cross-link during drying. A continuous network is formed having the great internal surface described above. Cross-linking of the silicon dioxide is increased.

In the production of aerogels, this process is prevented. For this, there are two fundamentally different paths according to the state of the art.

For one thing, super-critical drying methods are used. In this way, the effect of the capillary forces is hindered, because the liquid/gas phase transition is circumvented by a corresponding temperature/pressure regime. Herein, alcohols (methanol, ethanol, propanol) or liquid $CO_2$ are used as solvents, which must replace the original solvent, mostly $H_2O$, by means of exchange methods (S. S. Kistler, Phys. Chem. 36 (1932) 52-64, EP 171722; DE 1811353; U.S. Pat. No. 3,672,833; DE 39 24 244 A1; PCT/EP94/02822). The methods are very costly due to the autoclaves that are used.

On the other hand, there are methods according to the state of the art that allow sub-critical drying of aerogels. The core point of the method according to PCT/US94/05105 is modification of the contact angle between solvent and solid scaffolding. In this way, the capillary pressure is reduced and the structure of the moist gel is almost maintained. The contact angle is achieved by means of modification of the internal surface of the solid scaffolding in the moist gel. For this purpose, a reaction of the internal surface with $R_xSiX_y$ takes place. R is an organic group and X is a halogen. In this method, multiple solvent exchanges are required. In patent DE 19538333 A1, modification of the internal surface of the moist gel is implemented with $Si_{surface}O$—Z, wherein Z is any desired group that is supposed to prevent condensation of the internal surface during drying.

The methods used for the production of aerogels are not utilized within the scope of the present invention; in particular, gel formation does not occur.

It is the task of the present invention to produce materials having a defined degree of cross-linking of the silicic acid. From this, products such as microparticles, fibers or layers can be produced.

According to the invention, this task is accomplished in that further condensation is prevented in a sol once specific degrees of cross-linking of the silicic acid have been reached, particularly once the desired size of the silica gel clusters or the sol particles has been achieved by means of condensation, wherein the desired size of the silica gel clusters or sol particles preferably lies in the range of approximately 0.5 nm up to approximately 1000 nm, more preferably from 0.5 nm to 20 nm, more preferably from 0.5 nm to 10 nm, from 0.5 nm to 5 nm, from 0.5 nm to 4 nm, from 0.5 nm to 3 nm, from 0.5 nm to 2 nm or from 0.5 nm to 1 nm.

This happens in that a solution, particularly an aqueous solution of a soluble polymer, preferably polyvinylpyrrolidone (PVP), is added. A particularly preferred PVP is K90. Preferably, mixing takes place until the silicic acid structures are homogeneously distributed in the polymer. In particular, homogenization can be undertaken with an ultrasound homogenizer, for example. Mixing with a stirrer having high shear forces has equally proven to be effective.

In one embodiment, the pH is adjusted, after mixing, to approximately 6-8, particularly approximately pH 7 to approximately pH 7.4.

Surprisingly, in this connection, no precipitation of the silicic acid takes place. A gel is formed in which the $SiO_2$ condensation products and the molecules of the polymer (e.g. PVP) are homogeneously distributed.

This gel can be used, for example, in ointments or creams for wound treatment, for treatment of scars, or for cosmetic applications.

During drying, preferably during freeze-drying of the mixture, polymer and silicic acid polyhedral remain homogeneously distributed (see FIG. 1). During use as a wound dressing, the polymer can go into solution again, and thereby release the silicic acid polyhedrals.

Solutions capable of being spun can also be produced from a polymer/$SiO_2$/solvent mixture, wherein the solvent preferably is water. For this purpose, the ratio of polymer (preferably PVP), $SiO_2$ and solvent preferably is selected so that after mixing, the viscosity lies in the range of approximately 0.7-1.3 Pas, particularly at approximately 1 Pas. The solution can be pressed through nozzles immediately. In a spinning tower, the threads can dry in a tempered gas stream.

In this embodiment, in particular, a method for producing silicic acid structures having a low degree of cross-linking in a polymer matrix is subject matter of the invention, wherein:
a) a $SiO_2$ sol is produced in a solvent, wherein the sol particles preferably have a size of 0.5 nm to 4 nm,
b) a solution of a polymer in a solvent is produced,
c) the solution and the sol are homogeneously mixed.

In this connection, the solvent can be water or alcohol or a mixture of water and alcohol, wherein the alcohol is preferably ethanol.

In one embodiment of the invention, the pH of the sol is adjusted in step a) to the range of 6 to 8. In step b) the pH of the polymer solution can be adjusted to the range of 6 to 8.

In another embodiment of the invention, the sol is produced without adjusting the pH. The pH of the sol then preferably lies at approximately pH 2. The polymer solution for step b) can also be produced without adjusting the pH, wherein the pH of this solution then preferably lies, for example, in the case of PVP, at approximately 4. In this embodiment, the pH is preferably adjusted to 6-8 after mixing in step c), in particular to pH 7.

Mixing is in particular carried out until a homogeneous distribution of the silicic acid structures in the polymer has been reached. For example, mixing for approximately 6 min while stirring at 1000 rpm is possible.

Preferably, in the method according to the invention, $SiO_2$ and polymer are present in a mass ratio of 0.5/99.5 ($SiO_2$/polymer) to 50/50 (in step c) or in the end product).

Preferably, in the method according to the invention, the polymer is polyvinylpyrrolidone.

Preferably, in this method, the mixture from step c) is dried. The mixture can be cast into a mold and freeze-dried.

Preferably, so much solvent is removed from the mixture that the viscosity preferably lies in the range of 0.5 Pas to 1 Pas. As a result, threads can be spun that preferably are dried in a tempered gas stream. A nonwoven or woven fabric can be produced from these threads.

Within the scope of this method, the degree of cross-linking of the polymer, e.g. of the PVP, can be increased according to known methods, preferably by means of gamma irradiation.

A material that can be produced with a method according to the invention is also subject matter of the invention.

A material that can also be referred to as a biomaterial, and that is composed of $SiO_2$ structures, particularly polyhedral structures, which have a size of preferably 0.5 nm to 4 nm, and which are homogeneously distributed in a polymer matrix, is also subject matter of the invention. Preferably, the material is a hydrogel composed of $SiO_2$ structures, which preferably have a size of 0.5 nm to 4 nm, and which is made of a water-soluble polymer or comprises a water-soluble polymer, wherein polymer and $SiO_2$ structures are homogeneously distributed. The silicic acid structures having a low degree of cross-linking are, in particular, polyhedral structures or aggregates thereof. Aggregates of polyhedral structures are composed of polyhedral structures.

Preferably, in this material, $SiO_2$ and polymer are present in a mass ratio of 0.5/99.5 ($SiO_2$/polymer) to 50/50.

Preferably, in this material the polymer is polyvinylpyrrolidone, e.g. K90.

Preferably, this material is present as threads, which preferably form a nonwoven or woven fabric, as a film or as a sponge.

In one embodiment, this material (biomaterial), together with granulates that can be used or are used as bone replacement material, form a mass for filling bone defects (putty). Commercially available granulates can be used.

Such granulates are disclosed, for example, in WO 2004/103421 and EP 1 624 904. Nanobone (Artoss GmbH, Rostock, Germany) can be used, for example. Particularly preferred are highly porous bone replacement material granulates, particularly granulates on the basis of calcium phosphate, such as crystalline calcium phosphate that is embedded in a silicon dioxide xerogel matrix. Such granulates on the basis of calcium phosphate can particularly be obtained by means of production of the calcium phosphate by way of a precipitation reaction, in which the solution with the precipitated calcium phosphate is homogenized by stirring, a highly concentrated silicic acid solution is added, the mixture is fixed by means of the gel formation that subsequently occurs, and the mixture is transformed into a xerogel matrix by removing the solvent, wherein the calcium phosphate crystallites that lie in the xerogel matrix have a size of about 10 nm to about 2000 nm, and the granulate grains have a size of 1 μm to 1000 μm, and the silicon dioxide component lies in the range of 2 to 80 wt.-%, preferably in the range of 4 to 50 wt.-%, with reference to the total mass of the granulate grains. Furthermore, bone replacement materials in granulate form having a bovine origin (e.g. BioOss from the Geistlich company) or hydroxyl apatite ceramics (e.g. sintered hydroxyl apatite ceramics, such as Cerabone— aap Implantate AG, for example) can be used within the scope of the present invention. However, it must be taken into consideration that in the case of a putty based on water, no water-soluble granulates (e.g. β-TCP) can be used.

Use of the material for medical devices, particularly for those that have a supporting or shielding function and/or simultaneously serve as a supplier for the silicon dioxide that supports tissue regeneration, is also subject matter of the invention. Within the scope of the invention, the term medical device is used interchangeably with medical or pharmaceutical composition or medicament, because classification depends on national law, but does not change the substance of the invention.

An object of the invention is also use of the material as an ointment or cream, particularly for the treatment of wounds, scars, or for cosmetic applications.

An object of the invention is also a medical device that comprises the material according to the invention.

The present invention furthermore relates to methods for the production of a formable bone replacement material (putty), wherein a) a granulate that can be used as a bone replacement material is moistened with an aqueous solution, and b) the granulate that can be used as a bone replacement material is mixed with a biomaterial produced as described above. Granulates that can be used within the scope of this method comprise the granulates disclosed above.

In a particular embodiment, the mixture produced in step b) is freeze-dried, so that the user (for example a surgeon) can add an antibiotic solution (e.g. a gentamicin solution) to the sponge that formed, and thereby obtains a formable bone replacement material comprising antibiotics.

In another preferred embodiment, the formable bone replacement material (putty) is subjected to gamma irradiation at preferably 25-40 kGray, thereby forming elastic blocks.

Furthermore, a formable bone replacement material (putty) comprising a granulate that can be used as a bone replacement material and a biomaterial that has been produced as described above, is subject matter of the invention. Preferably, the formable bone replacement material (putty) is produced according to the methods described above.

The invention is explained and illustrated in the following examples, but not restricted by these in terms of its scope. Publications cited in this application are completely incorporated herein by reference.

FIGURE LEGENDS

The FIGURE shows, in various enlargements, scanning electron microscopy images of the sponge produced in Example 1 from polyvinylpyrrolidone and $SiO_2$ nanoparticles. A: scale=200 μm, B: scale=40 μm, C: scale=9 μm.

EXAMPLES

Example 1

With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 6% $SiO_2$ content is formed. 200 g of this sol are homogeneously mixed with 200 g of a twelve-percent PVP solution. For this purpose, ultrasound homogenization is used. Subsequently, the pH is adjusted to 7.4 with NaOH solution. The gel is placed in molds, for example with a size of 100 mm×100 mm×8 mm, and freeze-dried. Scanning electron microscopy images are shown in FIG. 1.

Example 2

Water-Soluble Nonwoven Fabric for Covering Wounds

With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 0.66% $SiO_2$ content is formed. 200 g of this sol are homogeneously mixed with 200 g of an aqueous 1.34% PVP K 90 solution (PVP—polyvinylpyrrolidone). For mixing, a stirrer is used at 1000 rpm. Subsequently, the pH is adjusted to 7.4±0.5 with NaOH solution. The gel is placed in molds with, for example, a size of 100 mm×100 mm×8 mm, and freeze-dried. A nonwoven fabric for wound covering is formed.

Example 3

Water-Insoluble Nonwoven Fabric for Wound Covering

With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 0.66% $SiO_2$ content is formed. 200 g of this sol are homogeneously mixed with 200 g of an aqueous 1.34% PVP K 90 solution (PVP—polyvinylpyrrolidone). For mixing, a stirrer is used at 1000 rpm. Subsequently, the pH is adjusted to 7.4±0.5 with NaOH solution. The gel is placed in molds with, for example, a size of 100 mm×100 mm×8 mm, and freeze-dried. Afterward, the non-woven fabric that has formed is exposed to saturated steam until it has absorbed 10% of its weight in water (swelling). Subsequent gamma irradiation (25-40 KGray) ensures cross-linking of the PVP in the nonwoven fabric. A nonwoven fabric for wound covering is formed.

Example 4

Gel-Like Wound Covering

With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 6% $SiO_2$ content is formed. 200 g of this sol are homogeneously mixed with 200 g of an aqueous 12% PVP K 90 solution (PVP—polyvinylpyrrolidone). For mixing, a stirrer is used at 1000 rpm. Subsequently, the pH is adjusted to 7.4±0.5 with NaOH solution. The gel is placed in molds with, for example, a size of 100 mm×100 mm×8 mm, and subjected to gamma irradiation of 25-40 kGray. A gel-like moist wound covering is formed.

Example 5

Bone Replacement Material Putty

With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 6% $SiO_2$ content is formed. 50 g of this sol are homogeneously mixed with 50 g of an aqueous 12% PVP K 90 solution (PVP—polyvinylpyrrolidone). For mixing, a stirrer is used at 1000 rpm. 62 g of a highly porous bone replacement material granulate (produced according to patent EP 1 624 904) are mixed with as much water that the internal pores are filled (in this case with 44 g water). The silica/PVP mixture and the moist granulate are homogeneously mixed. Subsequently, the pH is adjusted to 7.4±0.5 with NaOH solution. The mass is filled into typical applicators for bone replacement and sterilized in an autoclave.

Example 6

Bone Replacement Material Putty for Mixing with Commercially Available Antibiotic Solutions With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 6% $SiO_2$ content is formed. 50 g of this sol are homogeneously mixed with 50 g of an aqueous 12% PVP K 90 solution (PVP—polyvinylpyrrolidone). For mixing, a stirrer is used at 1000 rpm. 62 g of a highly porous bone replacement material granulate (produced as described in European Patent EP 1 624 904) are mixed with as much water that the internal pores are filled (in this case with 44 g water). The silica/PVP mixture and the moist granulate are homogeneously mixed. Subsequently, the pH is adjusted to 7.4±0.5 with NaOH solution. Cylinders are formed from the mass (10 mm diameter, 30 mm length). These cylinders are freeze-dried. Sponge-like dry elements are formed, which are introduced into applicators having an inside diameter of 10 mm. Steam-tight packaging in commercially available aluminum peel bags and gamma sterilization take place subsequently. For use, as much antibiotic solution is added to the sponge-like elements in the applicator that there is no air in the applicator (e.g. 1.5 ml Gentamicin-ratiopharm® 40 SF injection solution). The sponge-like cylinder swells and yields a kneadable mass (putty) for filling of bone defects.

Example 7

Elastic Molded Element of Bone Replacement Material

With a cation exchanger (e.g. LEWATIT®), the sodium ions are removed from sodium silicate solution having a $SiO_2$ content of 7%. A sol with a pH of approximately 2.4 is formed. After a determination of the content of solids, water is added until a sol having a 6% $SiO_2$ content is formed. 50 g of this sol are homogeneously mixed with 50 g of an aqueous 12% PVP K 90 solution (PVP—polyvinylpyrrolidone). For mixing, a stirrer is used at 1000 rpm. 62 g of a highly porous bone replacement material granulate (produced as described in European Patent EP 1 624 904) are mixed with as much water that the internal pores are filled (in this case with 44 g water). The silica/PVP mixture and the moist granulate are homogeneously mixed. Subsequently, the pH is adjusted to 7.4±0.5 with NaOH solution. The mass is placed into molds (blister packs 15×10×5 mm³). Steam-tight packaging in commercially available aluminum peel bags and gamma sterilization at preferably 25-40 kGray follow. Elastic blocks that are used for bone augmentation form.

The invention claimed is:

1. A biomaterial, composed of $SiO_2$ structures having a low degree of cross-linking, wherein said $SiO_2$ structures have a size of 0.5 nm to 1000 nm, and are distributed in a polymer matrix, wherein $SiO_2$ and polymer are present in a mass ratio of 0.5/99.5 ($SiO_2$/polymer) up to 50/50, but not including 50/50, wherein the polymer is polyvinylpyrrolidone.

2. The biomaterial according to claim 1, wherein said biomaterial is a hydrogel composed of $SiO_2$ polyhedral structures having a size of 0.5 nm to 4 nm, and a water-soluble polymer, wherein polymer and $SiO_2$ polyhedral structures are homogeneously distributed.

3. The biomaterial according to claim 1, wherein said biomaterial is present as threads, as a film, or as a sponge.

4. The biomaterial according to claim 1, which, together with granulates that can be used as bone replacement material, forms a mass for filling of bone defects (putty).

5. The biomaterial according to claim 1, for use as a medical device having a supporting or shielding function.

6. The biomaterial according to claim 1, for use for the treatment of wounds or scars or for cosmetic applications.

7. The biomaterial according to claim 1, wherein the biomaterial is made by a method for the production of silicic acid structures having a low degree of cross-linking in a polymer matrix, comprising:
   a) producing a $SiO_2$ sol in a solvent, wherein the sol particles have a size of 0.5 nm to 1000 nm,
   b) producing a solution of a polymer in a solvent,
   c) mixing the solution and the sol homogeneously, wherein $SiO_2$ and polymer are present in a mass ratio of 0.5/99.5 ($SiO_2$/polymer) up to 50/50, but not including 50/50.

8. A medical device or a nutritional supplement comprising the biomaterial according to claim 1.

9. A method for the production of a formable bone replacement material (putty), comprising
   a) moistening a granulate that can be used as a bone replacement material with an aqueous solution, and
   b) mixing the granulate that can be used as bone replacement material with a biomaterial according to claim 1.

10. The method according to claim 9, wherein the granulate that can be used as a bone replacement material comprises porous material.

11. The method according to claim 9, wherein the granulate that can be used as a bone replacement material comprises a calcium phosphate.

12. The method according to claim 9, wherein the granulate that can be used as a bone replacement material is of bovine origin.

13. The method according to claim 9, wherein the granulate that can be used as a bone replacement material comprises hydroxyl apatite ceramic.

14. The method according to claim 9, comprising freeze-drying the formable bone replacement material (putty).

15. The method according to claim 9, comprising subjecting the formable bone replacement material (putty) to gamma irradiation.

16. A formable bone replacement material (putty), comprising a granulate that can be used as bone replacement material and a biomaterial according to claim 1.

17. The biomaterial according to claim 5, wherein said polyvinylpyrrolidone is polyvinylpyrrolidone K90.

18. The biomaterial according to claim 3, wherein said threads form a nonwoven or woven fabric.

19. The method according to claim 15, wherein the formable bone replacement material is subjected to gamma irradiation at 25-40 kGray.

\* \* \* \* \*